United States Patent [19]

Roth et al.

[11] Patent Number: 5,418,006
[45] Date of Patent: May 23, 1995

[54] COATING OF SUBSTRATE SURFACES

[75] Inventors: Michael Roth, Burghausen; Christa Blämlhuber, Neuötting; Günther von Au; Loher Karl-Heinz, both of Burghausen, all of Germany

[73] Assignee: Wacker-Chemie GmbH, Munich, Germany

[21] Appl. No.: 8,025

[22] Filed: Jan. 25, 1993

[30] Foreign Application Priority Data

Jan. 23, 1992 [DE] Germany .................. 42 01 800.5

[51] Int. Cl.$^6$ .................. B05D 1/36; B05D 5/08
[52] U.S. Cl. .................. 427/154; 427/155
[58] Field of Search .................. 427/154, 416, 393.4, 427/155, 412, 334, 326, 408, 411, 412.2

[56] References Cited

U.S. PATENT DOCUMENTS

| | | | |
|---|---|---|---|
| 3,412,179 | 11/1968 | Kleiner | 427/393.4 |
| 3,467,612 | 9/1969 | Gagliardi | 427/393.4 |
| 4,125,673 | 11/1978 | Roth et al. | |
| 4,678,681 | 7/1987 | Obayashi et al. | 427/412 |
| 4,748,049 | 3/1988 | Charles et al. | 427/154 |
| 4,758,465 | 7/1988 | McKinney et al. | 427/412 |
| 4,943,475 | 7/1990 | Baker et al. | 427/412 |
| 4,973,510 | 11/1990 | Tanaka | 427/412 |
| 5,026,597 | 6/1991 | Franz et al. | |
| 5,143,949 | 9/1992 | Grogan et al. | 427/154 |

FOREIGN PATENT DOCUMENTS

| | | |
|---|---|---|
| 0107948 | 5/1984 | European Pat. Off. . |
| 2391784 | 12/1978 | France . |
| 2526287 | 9/1982 | France . |
| 2543514 | 10/1984 | France . |
| 3630520 | 12/1987 | France . |
| 1604562 | 12/1981 | United Kingdom . |

*Primary Examiner*—Diana Dudash
*Attorney, Agent, or Firm*—Martin Connaughton

[57] ABSTRACT

In the method for coating substrate surfaces which are not water-absorbent, the substrate surfaces are coated with an aqueous composition which comprises an aqueous solution, dispersion and/or emulsion of film-forming substances and water-repellent substances, in which the coating can be removed by treatment with water. The method is also suitable for coating porous, water-absorbent substrates if the substrates are treated with a water-repellent prior to coating with the aqueous composition.

8 Claims, No Drawings

COATING OF SUBSTRATE SURFACES

The invention relates to coated substrates and more particularly to a method for coating substrate surfaces with an aqueous composition of film-forming substances and water-repellent substances. The coating serves to protect and provides for ease of cleaning of the surfaces.

BACKGROUND OF THE INVENTION

The removal of contaminants, such as paint and pigeon droppings on substrates such as metals, plastic, painted surfaces, wood, concrete and stone, is accompanied by damage to the substrate surfaces when mechanical methods such as blasting with solid particles, are used.

In many cases the use of acid, bases or cleaning agents containing organic solvents for cleaning is not possible because they attack the substrate surface.

Cleaning with cold or hot water or steam, optionally under pressure, leads, in particular in the case of open-pore substrates, such as building materials, to severe loading of the substrate with water, with consequent damage.

Diverse known methods facilitate easier cleaning by means of a preventive treatment of the substrate surfaces.

It is known in practice to treat the substrate surfaces with a concentrated solution of organic polymers. These treatments, which are termed sealing, are ineffective and in the case of porous substrates block the pores, so that the permeability to air and water vapor is prevented. The sealings frequently also lead to adverse optical changes in the substrate surfaces, such as shine or dark discoloration. The solutions of organic polymers which are used in practice comprise predominantly organic solvents, which are a hazard to health and a fire hazard and pollute the environment. The removal of contaminants from substrate surfaces pretreated in this manner can usually be effected only by means of organic solvents.

An oil- and water-repellent impregnation which hinders the permeability to air and water vapor to a lesser extent is described in DE-A-25 26 287 (M. Roth and H. Glück; Wacker-Chemie GmbH, laid open on Dec. 30, 1976). With this method, the substrate surfaces are treated with a combination of organosilicon compounds and fluorine-containing organic compounds. However, the removal of contaminants requires the use of organic solvents.

A method for impregnating stone is disclosed in DE-C-36 30 520 (H. Ramesohl; published on Dec. 17, 1987), in which a detachable coating is applied which is receptive to paints but does not penetrate the impregnated stone. In the illustrative embodiment, the stone surface is impregnated to render it oil- and water-repellent and a coating composed of hard waxes liquefied by solvents is applied thereon. However, the wax coating impairs the permeability to air and water vapor to such an extent that the drying characteristics of the stone treated by this method are impaired, which can lead to damage. In addition, the detached wax, is a substance which pollutes the environment and must be disposed of as special waste.

It is also known in practice to apply aqueous solutions of polysaccharides to the substrate surface and to rinse off this coating, as required, together with the contaminants using water. This method has not proved suitable on outdoor surfaces exposed to rain, in particular, because of the solubility in water of the polysaccharide coating. The polysaccharide coating is neither water-repellent nor oil-repellent and does not protect the substrate against the uptake of water or organic liquids, such as fats and oils.

Therefore, it is an object of the present invention to provide a method for coating substrate surfaces which are not water-absorbent. Another object of the present invention is to coat substrate surfaces with a coating which is permeable to air and water vapor and is adequately resistant to weathering. Still another object of the present invention is to coat substrate surfaces with a coating which is easily removed, residue-free, together with the contamination without organic solvents. A further object of the present invention is to coat substrate surfaces with a coating which neither displays a shine nor dark discoloration. A still further object of the present invention is to provide a method for coating porous substrates to impart water-repellent properties thereto.

SUMMARY OF THE INVENTION

The foregoing objects and others which will become apparent from the following description are accomplished in accordance with this invention, generally speaking, by providing a method for coating substrate surfaces which are not water-absorbent, which comprises coating the substrate surfaces with an aqueous composition containing an aqueous solution, dispersion and/or emulsion of film-forming substances and water-repellent substances, in which the coating can be removed again by treatment with water.

DESCRIPTION OF THE INVENTION

The film-forming substances and the water-repellent substances are inert with respect to the substrates to be coated. In order that the coating can be removed again with water, the film-forming substances and the water-repellent substances must not crosslink, either with one another or with another constituent of the coating, or react with the substrate.

The aqueous compositions preferably are free of water-immiscible organic solvents. They comprise at most 10% by weight, and more preferably from 0 to 5% by weight, of water-miscible solvents or solvent mixtures, so that painted or impregnated substrate surfaces are not attacked. Physiologically acceptable solvents are preferred. If solvents are used, solvents or solvent mixtures which have a boiling point or boiling range of up to 160° C. under 0.1 MPa are preferred. Examples of such solvents are alcohols, such as methanol, ethanol, n-propanol, and iso-propanol; ethers, such as dioxane; glycol ethers, such as diethylene glycol dimethyl ether, ethylene glycol monomethyl ether and ethylene glycol monoethyl ether; ketones, such as acetone; and esters containing ether groups, such as the ethylene glycol monomethyl ether ester of acetic acid.

Preferred film-forming substances are organic synthetic polymers, such as polyvinyl chloride, polyethylene, polypropylene, polyvinyl acetate, polyvinyl alcohol, polycarbonate, polyacrylate, polymethacrylate, polymethylmethacrylate, polystyrene, polyacrylonitrile, polyvinylidene chloride, polyvinyl fluoride, polyvinylidene fluoride, polyvinylidene cyanide, polybutadiene, polyisoprene, polyether, polyester, polyamide, polyurethane, polyimide, silicones, polyvinylpyrrolidone, polyacrylamide, polyethylene glycol and derivatives thereof and similar polymers, including copolymers and also naturally occurring polymers, such as cellulose, starch, casein and natural rubber, and also semi-synthetic, high molecular weight compounds, such as cellulose derivatives, for example methylcellulose, hydroxymethylcellulose and carboxymethylcellulose and the sodium salts thereof.

Particularly preferred film-forming substances are water-soluble or water-swellable polymers, such as polysaccharides and polyvinyl alcohol.

Polysaccharides which can be used are, for example, cellulose, the above mentioned cellulose derivatives, cellulose ethers and cyclic polysaccharides, such as cyclodextrins.

The polyvinyl alcohol preferably has saponification numbers of from 800 to 0, corresponding to the consumption of mg KOH/1g of polyvinyl alcohol (the saponification number 0 corresponds to 100% OH groups). Saponification numbers of from 450 to 0, and in particular from 200 to 0, are particularly preferred. The viscosity of the 4% aqueous solution of a preferred vinyl alcohol is from 1 to 200 mPa.s, and in particular from 3 to 60 mPa.s, at 20° C. In addition to vinyl acetate units, the polyvinyl alcohol can also contain from 0 to 40 mol percent of the same or different units from the group comprising acrylic acid esters, methacrylic acid esters, vinyl esters, olefins, vinyl-aromatic compounds, ethylenically unsaturated carboxylic acids and their amides. However, a content of from 0 to 10 mol percent, and in particular from 0 to 1 mol percent, based on the total weight of the polymer, is preferred. Preferably, at least some of the ester groups of the above units are hydrolyzed to form the corresponding acid salt groups and vinyl alcohol groups.

Preferred (meth)acrylic acid esters which can be used in the form of homopolymers or as copolymers with vinyl acetate, which may be optionally hydrolyzed, are the esters of alcohols having from 1 to 10 carbon atoms, such as methyl (meth)acrylate, ethyl(meth)acrylate, propyl (meth)acrylate, butyl (meth)acrylate, 2-ethylhexyl (meth)acrylate or lauryl (meth)acrylate.

Preferred vinyl esters which may be mentioned are the esters of alkylcarboxylic acids having from 1 to 15 C atoms, such as vinyl acetate, vinyl propionate, vinyl butyrate, vinyl 2-ethylhexanoate, vinyl laurate or 1-methylvinyl acetate (isopropenyl acetate).

Suitable olefins are ethylene, propylene or butadiene. Preferred vinyl aromatic compounds are styrene or vinyltoluene.

Examples of ethylenically unsaturated carboxylic acids and their amides are acrylic acid, methacrylic acid, itaconic acid, fumaric acid, maleic acid and their monoamides and diamides, and in particular (meth)acrylic acid, (meth)acrylamide and N-methylolacrylamide.

Examples of copolymers which, optionally may be completely or partially hydrolyzed, can be used as film-forming substances are vinyl acetate/ethylene copolymers, vinyl acetate/ethylene/N-methylol(meth)acrylamide terpolymers, alkyl acrylate/N-methylol(meth)acrylamide copolymers and vinyl acetate/ethylene/acrylate copolymers or vinyl acetate/acrylate copolymers, which optionally have an N-methylol(meth)acrylamide content.

Film-forming substances from which aqueous solutions can be prepared are preferably used.

The aqueous composition comprises preferably from 0.1 to 20% by weight, and in particular from 1.0 to 10% by weight, of film-forming substances.

Any desired water-repellent substances can be used in the method of this invention. If the water-repellent substances are not soluble in water and not emulsifiable, they must be used in such a finely divided form that they are dispersible. The finely divided water-repellent substances preferably have a surface area of at least 20 $m^2/g$.

Water-repellent substances which can be used in the method of this invention are, for example, inorganic substances which have been rendered hydrophobic or optionally fluorinated waxes, paraffins, carboxylic acid salts or organic or silicon-organic polymer compounds.

Examples of suitable inorganic substances rendered hydrophobic are quartz, diatomaceous earth, calcium silicate, zirconium silicate, zeolites, montmorillonites, such as bentonites, metal oxide powders, such as aluminum oxide, titanium oxide or zinc oxide or their mixed oxides, barium sulfate, calcium carbonate, gypsum, powdered glass, pyrogenic and precipitated silica and silicon/aluminum mixed oxides. The said inorganic substances can be rendered hydrophobic, for example by treatment with organosilanes or organosiloxanes or by esterification of hydroxyl groups to alkoxy groups. Pyrogenic and precipitated silicas are preferred since these are readily dispersible and the coating remains translucent.

Suitable waxes are, for example, naturally occurring waxes, such as vegetable waxes, for example candelilla and carnauba wax; animal waxes, for example beeswax and lanolin; mineral waxes, for example ceresin and ozokerite; chemically modified naturally occurring, in particular fluorinated, waxes and synthetic waxes, for example polyethylene waxes and silicone waxes.

Suitable carboxylic acid salts are, in particular, the salts of monobasic or polybasic carboxylic acids having from 8 to 50 carbon atoms per carboxyl group. The salts of fluorinated carboxylic acids are preferred, especially if these comprise a perfluoroalkyl radical having at least 4 carbon atoms. Examples of preferred monovalent fluorinated carboxylic acid salts are the alkali metal salts of arylcarboxylic acids, such as benzoic acids or naphthoic acids comprising one or two perfluoroalkyl radicals having preferably from 4 to 18 carbon atoms.

Fluorinated organic polymer compounds which can be used in the method of this invention are, for example, all compounds which heretofore have been, or could have been used, for rendering organic substances, such as organic fibers, and inorganic substances water-repellent and oil-repellent. Examples of such compounds are polymers produced from monomers including at least some fluorine-containing monomers, such as polytetrafluoroethylene, copolymers of tetrafluoroethylene and hexafluoropropylene, polyvinyl fluoride, polyvinylidene fluoride, polytrifluorochloroethylene, copolymers of trifluorochloroethylene and other monomers, such as vinylidene fluoride, vinyl chloride, vinyl acetate, methyl methacrylate or styrene; and fluorinated acrylic resins, such as homopolymers and copolymers of perfluoroalkyl group-containing acrylic acid esters and methacrylic acid esters with acrylic acid and methacrylic acid and the derivatives thereof mentioned in connection with the film-forming substances.

Preferred examples of fluorinated acrylic resins are poly-1,1-dihydroperfluorobutyl acrylate and the copolymers composed of N-butylacrylate, N-methylolacrylamide and at least 35% by weight of 1,1,2,2-tetrahydroperfluoro-$C_1$- to $C_{16}$-alkyl methacrylate having a straight alkyl chain which are described in DE-C-25 26 287.

Preferred fluorinated acrylic resins are those which have at least a sufficient number of carboxylic acid salt groups to render the resins water-soluble. Examples of such water-soluble resins are the alkali metal salts of the copolymers of the above mentioned acrylates, methacrylates, acrylic acid and methacrylic acid, which preferably have a fluorine content of at least 20% by weight.

Examples of other fluorinated organic polymer compounds are organic synthetic polymers fluorinated after polymerization, such as the polymers mentioned in connection with the film-forming substances, which are fluorinated in the side chains or in the main chains. The polymers fluorinated after polymerization preferably have a fluorine content of at least 10% by weight. Polyurethane resins having a fluorine content of 25-35% by weight are particularly preferred.

The fluorinated organic polymer compounds are not only water-repellent but, in addition, are also oil-repellent.

If the water-repellent substances are not soluble in water, water-soluble film-forming substances which are able to disperse or emulsify the water-repellent substances are preferably used.

Preferably, the aqueous composition comprises from 0.1 to 20% by weight, and in particular from 1.0 to 10% by weight, of water-repellent substances.

Suitable anionic dispersing agents and emulsifiers used in the method of this invention are, for example:

p1 1. Alkyl sulfates, especially those having a chain length of from 8 to 18 C atoms, and alkyl sulfates and alkyl ethersulfates having from 8 to 18 C atoms in the hydrophobic radical and 1 to 40 ethylene oxide (EO) or propylene oxide (PO) units.
2. Sulfonates, especially alkylsulfonates having from 8 to 18 C atoms, alkylarylsulfonates having from 8 to 18 C atoms, taurides, and esters and half-esters of sulfosuccinic acid with monohydric alcohols or alkylphenols having from 4 to 15 C atoms; these alcohols or alkylphenols can optionally also be ethoxylates having from 1 to 40 EO units.
3. Alkali metal salts and ammonium salts of carboxylic acids having from 8 to 20 C atoms in the alkyl, aryl, alkaryl or aralkyl radicals.
4. Phosphoric acid partial esters and the alkali metal and ammonium salts thereof, especially alkyl phosphates and alkaryl phosphates having from 8 to 20 C atoms in the organic radical, and alkyl ether phosphates and alkaryl ether phosphates having from 8 to 20 C atoms in the alkyl or alkaryl radical and 1 to 40 EO units.

Suitable nonionic dispersing agents and emulsifiers which can be used in the method of this invention are, for example:
1. Alkyl polyglycol ethers, preferably those having from 8 to 40 EO units and alkyl radicals of from 8 to 20 C atoms.
2. Alkylaryl polyglycol ethers, preferably those having from 8 to 40 EO units and from 8 to 20 C atoms in the alkyl and aryl radicals.
3. Ethylene oxide/propylene oxide (EO/PO) block copolymers, preferably those having from 8 to 40 EO and PO units.
4. Fatty acids having from 6 to 24 C atoms.
5. Natural substances and derivatives thereof, such as lecithin, lanolin, saponins and cellulose; cellulose alkyl ethers and carboxyalkylcelluloses, the alkyl groups of which in each case have up to 4 carbon atoms.
6. Polar group-containing straight-chain organo(poly)siloxanes, especially those containing alkoxy groups having up to 24 C atoms and/or up to 40 EO and/or PO groups.
7. The polyvinyl alcohol described above.

Suitable cationic dispersing agents and emulsifiers which can be used in the method of this invention are, for example:

1 1. Salts of primary, secondary and tertiary fatty amines having from 8 to 24 C atoms with acetic acid, sulfuric acid, hydrochloric acid and phosphoric acids.
2. Quaternary alkyl benzene ammonium salts, in particular those in which the alkyl group has from 6 to 24 C atoms, especially the halides, sulfates, phosphates and acetates.
3. Alkylpyridinium, alkylimidazolinium and alkyloxazolinium salts, in particular those in which the alkyl chain has up to 18 C atoms, especially the halides, sulfates, phosphates and acetates.

In addition to the above constituents, the aqueous composition can, for specific purposes, also contain surfactants, biocides, aroma substances and/or dyes. The biocides and surfactants are preferably added in amounts of from 0.05 to 0.5% by weight. Suitable biocides are, for example, fungicides, bactericides, algicides and microbicides.

Surfactants coat lipophilic contaminants in the coatings and by this means, together with the above mentioned dispersing agents and emulsifiers which are optionally present, prevent the contaminants coming into contact with the substrate.

Suitable surfactants are, in particular: nonionic surfactants, such as oxalkylates, that is reaction products of ethylene oxide and/or propylene oxide with alcohols, alkylphenols or fatty acids, fatty acid ethanolamides, fatty acid glycerol esters and fatty amines; esters of fatty acids with polyhydroxy compounds; block copolymers of propylene oxide and ethylene oxide; cationic surfactants, such as quaternary ammonium compounds in which the nitrogen atom of the ammonium group is bonded to alkyl, alkaryl, alkylenehydroxy, alkylenealkoxy and alkyleneamino groups; imidazolinium salts alkylated in the C and/or N atoms and in which the anion is halide, sulfate, phosphate, or acetate; anionic surfactants, such as carboxylates, in particular alkali metal salts or ammonium salts of fatty acids or of their (poly-)oxyalkylene esters; sulfonates, especially alkylbenzenesulfonates, alkylnaphthalene sulfonates, alkanesulfonates, olefinsulfonates, α-sulfo fatty acid esters, alkyl sulfosuccinates, alkoxy-, acyloxy- and acylaminoalkanesulfonates; sulfates, especially primary and secondary alkyl sulfates and salts of the sulfuric acid half-esters of alkyl oligoglycol ethers or alkylaryl oligoglycol ethers; phosphonates and phosphates, especially alkali metal and/or ammonium salts of these compounds, which comprise alkyl and/or alkaryl groups; amphoteric surfactants, such as amino carboxylic acids; silicone surfactants, especially polymethylsiloxanes comprising ethyleneoxy, propyleneoxy, alkoxy and ammonium groups; and fluoro-surfactants, especially fluoroalkanecarboxylic acids.

The coatings applied by the method of this invention can be removed again, residue-free, by for example, spraying with water. The use of pressure and the use of heated water, preferably at 50° to 95° C., accelerates the removal of the coating. Despite the removability with water, the coatings applied by the method of this invention are adequately resistant to weathering to enable them to remain on the surface for a period of months.

The method of this invention is suitable for coating porous, water-absorbent substrates if the latter are provided with a water-repellent treatment prior to coating with the aqueous composition. The coating is then easily removed, residue-free, with water.

Since the coating is permeable to water vapor, a system which is permeable to water vapor overall can be obtained if impregnated with a substance which is likewise permeable to water vapor. Examples of known impregnating agents for porous, water-absorbent substrate surfaces which are suitable for this purpose are the organosilicon compounds listed in DE-A-25 58 184 (M. Roth; Wacker-Chemie GmbH, laid open on Jul. 7, 1977), such as alkoxy containing organosilanes, partial hydrolysis products thereof, reaction products of organochlorosilanes with ethylene glycol or diethylene glycol, organopolysiloxanes comprising alkoxy groups and optionally hydroxyl groups, and alkali metal hydrocarbon siliconates containing alkoxy groups and optionally hydroxyl groups.

Other suitable impregnating agents are aqueous emulsions of alkyl trialkoxysilanes and nitrogen-free and basic nitrogen-containing polyorganosiloxanes comprising alkoxy groups disclosed in U.S. Pat. No. 4,661,551 (H. Mayer et al., Wacker-Chemie GmbH, issued on Apr. 28, 1987). Aqueous emulsions of alkyltrialkoxysilanes for the water-repellent impregnation of building materials are disclosed, inter alia, in U.S. Pat. No. 4,877,654 (M. E. Wilson, PCR, Inc., issued on Oct. 31, 1989). Emulsions of alkoxy group-containing organopolysiloxanes for rendering building materials hydrophobic are described in U.S. Pat. No. 4,704,416 (H. Eck and M. Roth; Wacker-Chemie GmbH, issued on May 3, 1988).

Treatment of the water-absorbing substrates with oleophobic impregnating agents impairs their gas permeability and in particular their permeability to water vapor and is therefore not preferred in the case of building materials.

The coating applied by the method of this invention makes it possible to remove contaminants, such as paint, tar, diesel soot and pigeon droppings, from, for example, metal surfaces, glass surfaces, plastic surfaces, including elastomers and thermoplastics, and painted surfaces, impregnated surfaces of unpainted or painted wood, concrete, natural or synthetic stone, plaster and ceramic surfaces. Posters can also easily be stripped off after moistening. Self-adhesive stickers can be stripped off easily from the coated substrate surfaces.

Unless otherwise specified, in the following examples,
(a) all quantity and concentration data are by weight;
(b) all pressures are 0.10 MPa (abs.); and
(c) all temperatures are 20° C.

Examples 1

A mixture containing 4.0 parts of polyvinyl alcohol having a saponification number of 140, which as a 4% solution has a viscosity of 13 mPa.s at 20° C., 5.0 parts of a 20% solution of a 37% fluorine-containing potassium salt of an arylmonocarboxylic acid having a perfluoroalkyl radical of, on the average, 7 carbon atoms bonded to the aryl group (Scotchgard FX 3535 from 3M Comp, USA) in water/isopropanol/butyl Cellosolve ® (30/10/40) and 91.0 parts by weight of water was applied using a brush to one half of a PVC sheet, a Plexiglass sheet, steel sheet, aluminum sheet and anodized aluminum sheet.

After 3 days the two halves of the sheets were sprayed with vehicle paint and with a bitumen-based vehicle underbody protection.

After an additional 2 days the surfaces treated in this manner were treated with warm water under gentle pressure.

Both contaminants were removed residue-free from all treated substrates after treating with water under gentle pressure; however no cleaning effect could be achieved in the case of the untreated surfaces, even after prolonged treatment with warm water.

Example 2

Ceramic roof tiles, sand-lime bricks, fiber-cement boards, plaster boards and natural stone slabs were first treated with a silicone solution which imparts a hydrophobic effect to the treated surfaces. After 24 hours the mixture specified in Example 1 was applied with a brush to half of each of the building materials pretreated in this manner. After an additional 24 hours, the contaminants specified in Example 1 and also felt-tip pen graffiti were applied to both halves of the samples.

After a drying time of 4 days, the building materials were treated with hot water under low pressure. In the case of the untreated surfaces all three contaminants were not removed, while the contaminants on the surfaces treated according to this invention could be removed from all the building materials after a brief period of treatment with the hot water.

Example 3

In order to test the resistance to weathering of the coatings applied according to this invention, the building materials described in Example 2, which previously had been rendered hydrophobic using a silicone solution, were treated with a 4% solution of polyvinyl alcohol (PVA) or with the mixture used according to the invention and described in Example 1. After two days, 0.1 ml of water and 0.1 ml of edible oil was dripped onto the two surfaces.

Assessment of the water and oil drops:
The building materials treated with the pure PVA solution could spontaneously be wetted very well with water. The edible oil was very rapidly absorbed.
The coatings applied according to this invention showed incipient wetting only after 2 hours. The edible oil had still not been absorbed after 24 hours.
The highly hydrophobic and oleophobic action of the coating applied according to this invention prevents rapid weathering by precipitation.

Example 4

About 97 parts of a 4% aqueous solution of a carboxymethylcellulose, which as a 2% solution has a viscosity of 25-32 mPa.s at 20° C., and a 2% aqueous solution of a carboxymethylcellulose, which has a viscosity of 200-330 mPa.s at 20° C., was mixed with, in each case, 3.0 parts of a paste which contains 40% by weight of fluorinated polyurethane which has a fluorine content of 31% by weight, 40% of water and 20% of diethylene glycol monobutyl ether.

These mixtures were applied with a brush to, in each case, one half of square tiles and sand-lime bricks previously rendered water-repellent by impregnation with a silicone solution. After 4 days all the tiles were sprayed with a vehicle paint. Two days later the samples were treated with hot water under low pressure. While no cleaning whatsoever could be observed, even after a prolonged period of action of the water on the halves of the tiles impregnated only with water-repellent, residue-free removal of the paint coat could be achieved very rapidly on the halves of the tiles treated according to this invention.

Example 5

About 95.0 parts of a 5% aqueous solution of a hydroxymethylcellulose, which as a 2% aqueous solution has a viscosity of 20 mPa.s at 20° C., were mixed with 5.0 parts of a 30% anionic dispersion of the potassium salt used in Example 1 in 60% of water and 10% of ethylene glycol.

This mixture was sprayed onto sheet steel and onto a glass plate. After 24 hours, vehicle paint and a bitumen-based vehicle underbody protection were sprayed on the substrates. Two days after spraying on the paint and the underbody protection, hot water under low pressure (tap water pressure) was applied to the surfaces prepared in this manner. While the contaminants were very easily removed residue-free from the samples treated according to this invention, the samples without the pretreatment of this invention could not be cleaned, even after prolonged action of the hot water.

What is claimed is:

1. A method for protecting and providing for ease of cleaning of a porous, water-absorbent substrate comprising the steps of (1) treating the substrate with an impregnating agent which renders the substrate water repellent, selected from the group of organosilicon compounds consisting of alkoxy containing organosilanes and partial hydrolysis products thereof, reaction products of organochlorosilanes with ethylene glycol or diethylene glycol and alkoxy containing organopolysiloxanes and alkoxy containing alkali metal hydrocarbon siliconates, and subsequently forming a coating by applying to the substrate surface an aqueous composition containing an aqueous solution, dispersion and/or emulsion of a film-forming substance and a water-repellent substance selected from the group consisting of hydrophobic inorganic substances, paraffins, fluorinated or non-fluorinated waxes, carboxylic acid salts, organic polymers and silicone waxes, in which the coating can be removed with water.

2. The method of claim 1, wherein the film-forming substance is an organic polymer.

3. The method of claim 1, wherein the film-forming substance is a polysaccharide.

4. The method of claim 1, wherein the film-forming substance is polyvinyl alcohol.

5. The method of claim 1, wherein the aqueous composition contains from 0.1 to 20% by weight of a film-forming substance.

6. The method of claim 1, wherein the water-repellent substance is a fluorinated carboxylic acid salt.

7. The method of claim 1, wherein the aqueous composition also contains compounds selected from the group consisting of surfactants, biocides, aroma substances and dyes.

8. The method of claim 1, wherein the aqueous composition contains 0.1 to 20% by weight of said water-repellent substance.

* * * * *

UNITED STATES PATENT AND TRADEMARK OFFICE
CERTIFICATE OF CORRECTION

PATENT NO. : 5,418,006
DATED : May 23, 1995
INVENTOR(S) : Michael Roth, Christa Blümlhuber, Günther von Au and Karl-Heinz Loher It is certified that error appears in the above-indentified patent and that said Letters Patent is hereby corrected as shown below:

On cover page, column 1, under "Inventors", delete "Blämlhuber" and insert in lieu of --- Blümlhuber ---.

In claim 1, column 10, line 9, after "and", delete "subsequently forming" and on line 11, insert --- (2) subsequently forming ---.

Signed and Sealed this

Fifth Day of September, 1995

Attest:

BRUCE LEHMAN

Attesting Officer

Commissioner of Patents and Trademarks